(12) United States Patent
Agarwal et al.

(10) Patent No.: US 8,288,571 B2
(45) Date of Patent: Oct. 16, 2012

(54) PROCESS FOR PREPARING AROMATIASE INHIBITOR EXEMESTANE

(75) Inventors: Virendra Kumar Agarwal, Gujarat (IN); Manoj Kumar Singh, Gujarat (IN); Anant M. Patel, Gujarat (IN); Kirtipalsinh Solanki, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 126 days.

(21) Appl. No.: 12/810,208

(22) PCT Filed: Nov. 28, 2008

(86) PCT No.: PCT/IN2008/000790
§ 371 (c)(1),
(2), (4) Date: Aug. 18, 2010

(87) PCT Pub. No.: WO2009/093262
PCT Pub. Date: Jul. 30, 2009

(65) Prior Publication Data
US 2010/0311993 A1   Dec. 9, 2010

(30) Foreign Application Priority Data

Jan. 21, 2008   (IN) .......................... 144/MUM/2008

(51) Int. Cl.
*C07J 1/00* (2006.01)
(52) U.S. Cl. ....................................................... 552/623
(58) Field of Classification Search ................... 552/623
See application file for complete search history.

(56) References Cited

U.S. PATENT DOCUMENTS 4,808,616 A   2/1989   Buzzetti et al.

OTHER PUBLICATIONS

Mascheroni et al. CAS: 151:358974, 2006.*

* cited by examiner

*Primary Examiner* — Rei-tsang Shiao
(74) *Attorney, Agent, or Firm* — Ladas & Parry LLP

(57) ABSTRACT

The present invention discloses modified process for preparing aromatase inhibitor Exemestane involving suitable oxidizing agents in suitable solvents.

8 Claims, No Drawings

PROCESS FOR PREPARING AROMATASE INHIBITOR EXEMESTANE

FIELD OF INVENTION

The present invention discloses modified process for preparing aromatase inhibitor Exemestane.

BACKGROUND OF THE INVENTION

Exemestane is chemically described as 6-methylene-androsta-1,4-diene-3,17-dione and also sold as Aromasin®; it has the following formula (I).

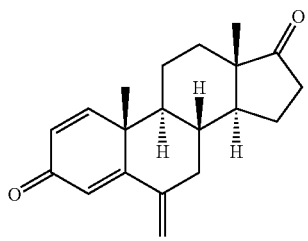

Formula (I)-Exemestane

Molecular formula of Exemestane is $C_{20}H_{24}O_2$. Molecular weight is 296.4. Exemestane is an oral steroidal aromatase inhibitor (also known uniquely as an aromatase inactivator) used in the adjuvant treatment of hormonally-responsive also called estrogen-responsive breast cancer in postmenopausal women.

The main source of estrogen is the ovaries in premenopausal women, while in post-menopausal women most of the body's estrogen is produced in the adrenal gland from the conversion of androgens into estrogen by the aromatase enzyme. Exemestane is an irreversible, steroidal aromatase inactivator, structurally related to the natural substrate androstenedione. It acts as a false substrate for the aromatase enzyme, and is processed to an intermediate that binds irreversibly to the active site of the enzyme causing its inactivation. In other words, the Exemestane, by being structurally similar to the target of the enzymes, permanently binds to those enzymes, thereby preventing them from ever completing their task of converting androgens into estrogens.

U.S. Pat. No. 4,808,616 is the product patent of Exemestane. The said patent relates to 6-substituted androsta-1,4-diene-3,17-diones, which are useful for the treatment of cancer. The general process for the preparation of 6-substituted androsta-1,4-diene-3,17-diones is shown in below scheme:

Scheme 1

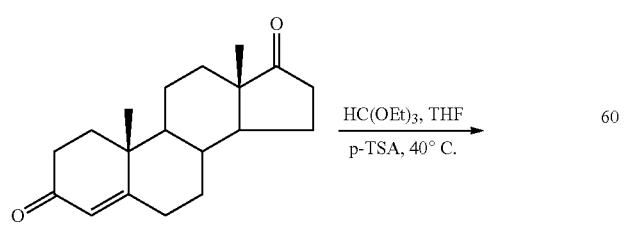

Androst-4-ene-3,17-dione
(AD)

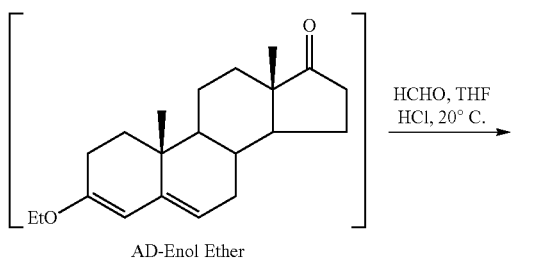

AD-Enol Ether

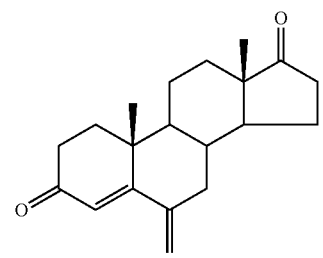

AD-6-Methylene

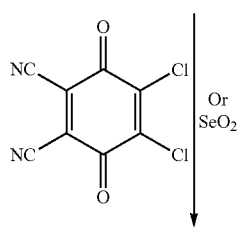

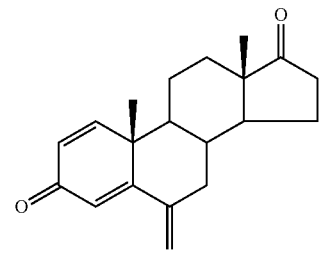

EXEMESTANE

The dehydrogenation of AD-6-Methylene was carried out by using dichlorodicyanobenzoquinone (DDQ) and selenium dioxide.

U.S. Pat. No. 4,876,045 relates to the process for the preparation of Exemestane and its analogous compound by treating androsta-1,4-dien-17β-ol-3-one with amine to form 17β-ol-3-one compound which is further oxidized to proexemestane using Jone's reagents as shown in below scheme 2:

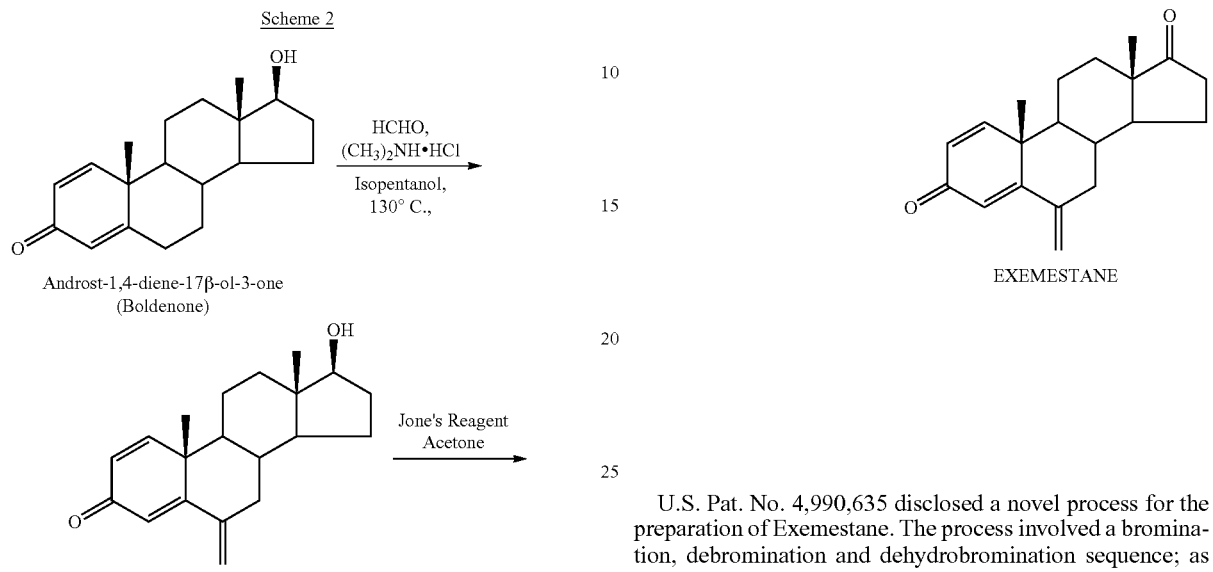

U.S. Pat. No. 4,990,635 disclosed a novel process for the preparation of Exemestane. The process involved a bromination, debromination and dehydrobromination sequence; as shown in below scheme:

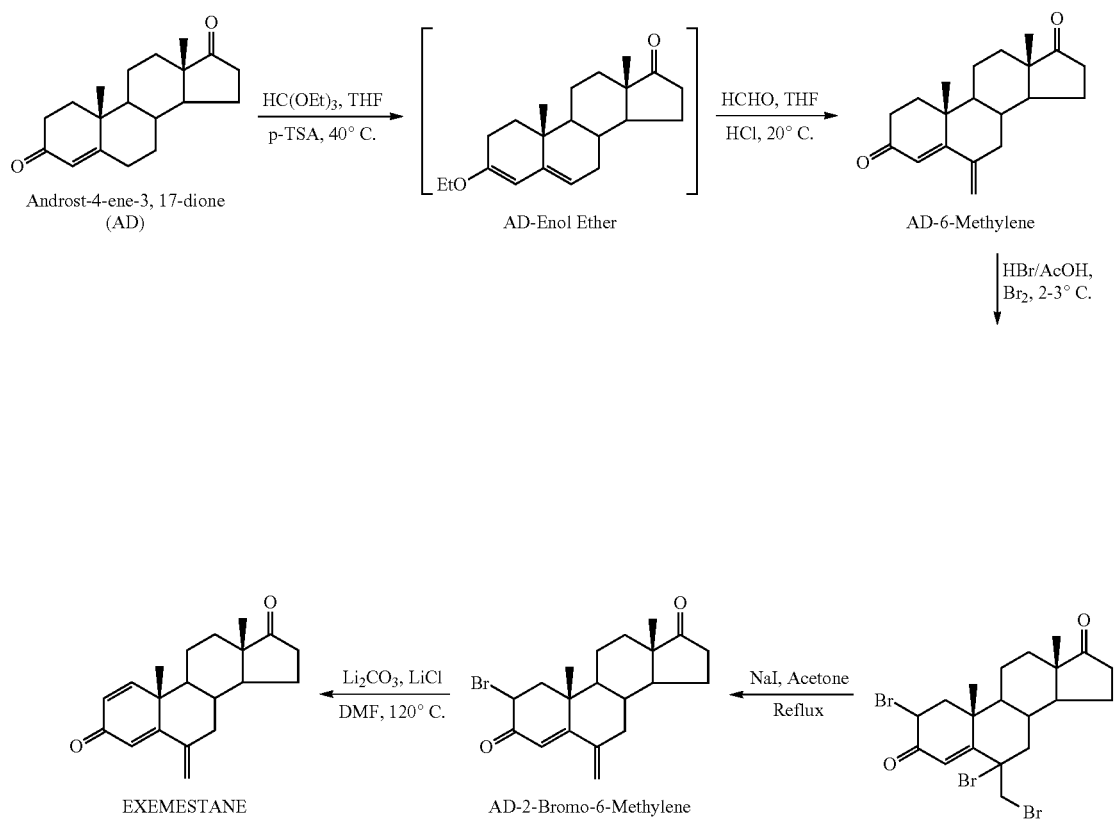

WO 2001004342 relates to the process for the preparation of Exemestane by using dehydrogenating enzymes.

WO 2005070951 describes novel process for the preparation of Exemestane. Androst-1,4-diene-3,17-dion is reacted with pyrrolidine in formaline to give an intermediate which is further treated with triethyl amine and methane sulfonyl chloride in diluted methanol and subsequently reacted with NaOH or KOH to give Exemestane as shown in below scheme:

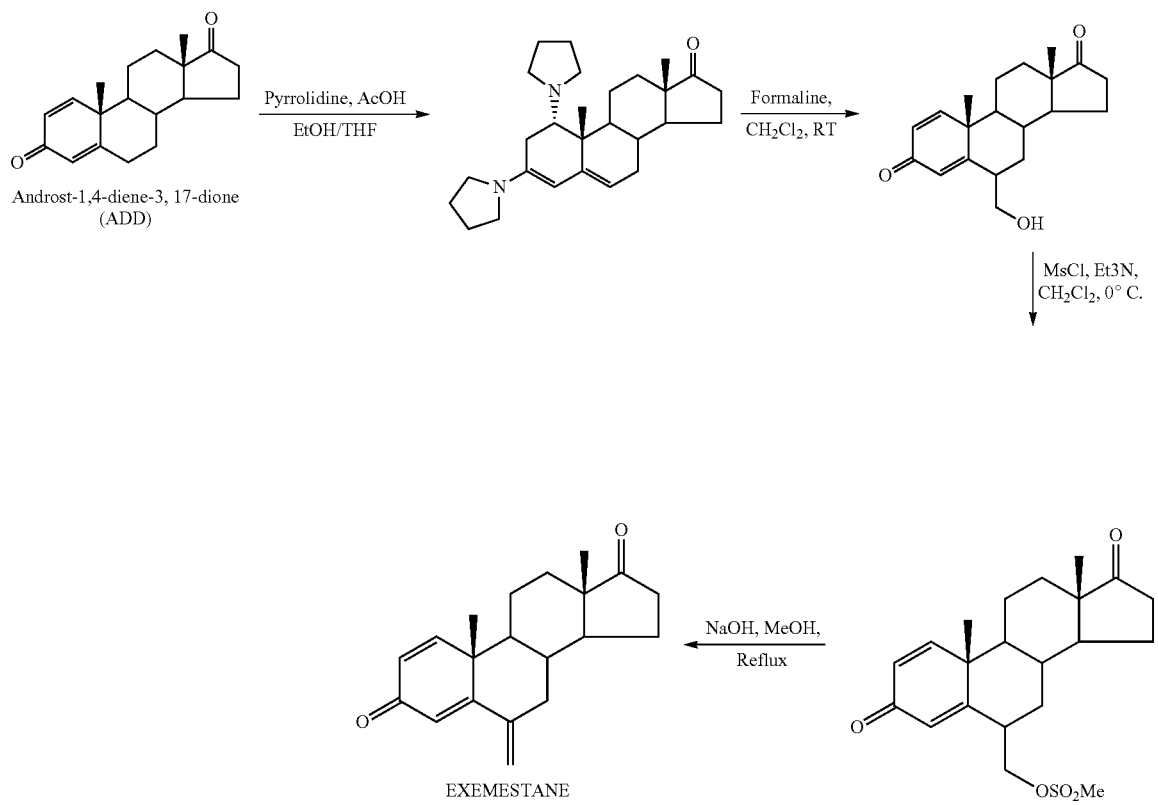

There is a need to develop a modified process for preparing Exemestane which give better yields and improved purity. We herein disclose a modified process for preparing Exemestane which give better yield with improved purity.

OBJECTS OF THE INVENTION

It is an object of the present invention to provide a modified process for preparing Exemestane.

DETAILED DESCRIPTION

There are several existing processes for preparing Exemestane by oxidizing the intermediate (II) using different oxidizing agents and in different solvents.

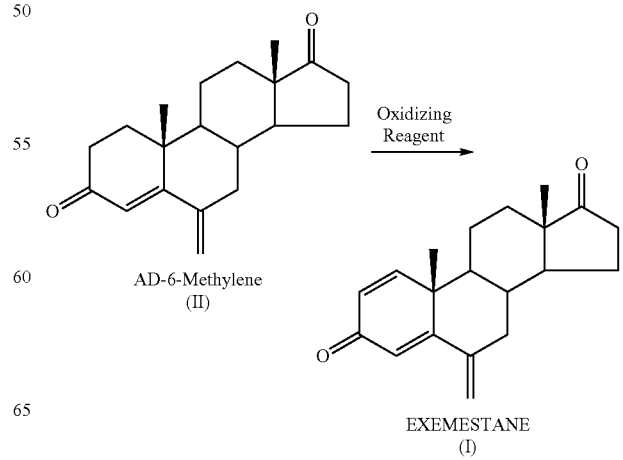

However, the present inventors found that these have some drawbacks. Some of them are listed below in the following table: 1

| Sr. No. | Intermediate (II) | Oxidizing Reagent | Solvent (Volume) | Temp. (° C.) | Results |
|---|---|---|---|---|---|
| 1 | 5 gm | DDQ | NMP (10 Volume) | 90-100 | Only 50% reaction, various impurities formed, product could not isolated. |
| 2 | 5 gm | DDQ | DMSO (10 Volume) | 90-100 | Product was not formed, only impurities were observed on TLC. |
| 3 | 5 gm | DDQ | Toluene (10 Volume) | 110-115 | Only 40% reaction, various impurities formed, product was difficult to isolate. |
| 4 | 5 gm | DDQ | 1,4-Dioxane (10 Volume) | 110-120 | Reaction stops after 80% conversion on TLC, product (1.5 gm) was isolated with only 56% HPLC purity. 8.53% Input remains unreacted. |
| 5 | 5 gm | DDQ (p-TSA as catalyst) | 1,4-Dioxane (10 Volume) | 110-120 | Product isolated (1.7 gm), 68% purity on HPLC. 2% Input remains unreacted. |
| 6 | 5 gm | Chloranil | Toluene (10 Volume) | 110-115 | Product not formed. |
| 7 | 5 gm | Chloranil | DMSO (10 Volume) | 90-100 | Product formed but difficult to isolated. |
| 8 | 25 gm | Chloranil | NMP (10 Volume) | 75-80 | Reaction completed in 15 hours. HPLC Purity: 97%; Yield: 13 gm |
| 9 | 25 gm | Chloranil | NMP (3 Volume) | 100-110 | Reaction completed in 2 hours. HPLC Purity: 95.3%; Yield: 11 gm |

NMP: N-methylpyrrolidine,
DMSO: Dimethyl sulfoxide,
DDQ: Dichlorodicyanoqiunone

Particularly, DDQ is used as an oxidizing agent in solvents like NMP, DMSO, 1,4-dioxane and toluene only 50-80% reaction conversion is possible, various impurities were formed and product could not isolated. Corresponding yield and purity data are given in Table No. 1. When Chloranil is used as an oxidizing agent and toluene use as solvent, product was not formed.

The present inventors have surprisingly found out that when Chloranil is used as an oxidizing agent, in suitable solvents, Exemestane was obtained in good yield and purity. The modified process for preparing Exemestane is described in the following Sheme 5.

Scheme 5

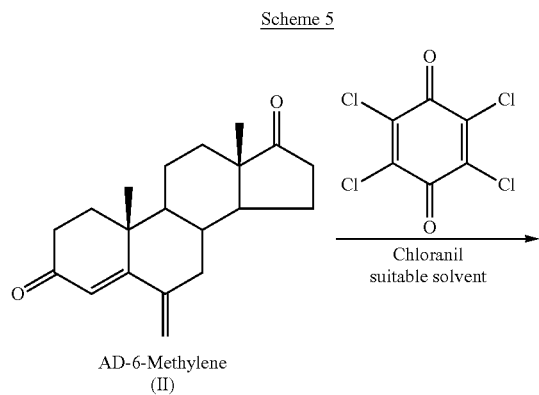

AD-6-Methylene
(II)

-continued

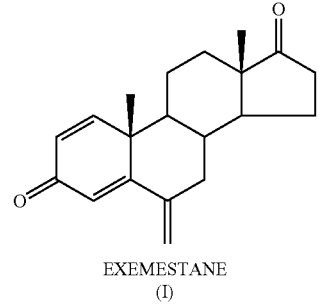

EXEMESTANE
(I)

Suitable solvents used in above step may be selected from NMP, DMSO and the like or mixtures thereof most preferably NMP. The oxidizing agent used in above step Chloranil, was charged in to the reaction mixture at room temperature.

The reaction was carried out at temperature ranging from at 50-120° C. and more preferably the reflux temprature is 80 to 110° C.

The reaction time for above step is about 1-20 hours and more preferably reaction hour is 10-18 hours.

The invention is further described by the following non-limiting example, which is provided for illustration only and should not be construed to limit the scope of invention.

EXAMPLE 1

Process for the Preparation of 6-Methylen-androst-1,4-diene-3,17-dione (Exemestane)

6-Methylen-androst-4-ene-3,17-dione (5.0 gm) was dissolved in N-methylpyrrolidine (25 mL) at RT & to it was charged Chloranil (12.37 gm) at RT. The reaction mass was heated to 75 to 80° C. for 18 hours. The progress of the reaction is monitored on TLC. The reaction mass was cooled down to room temperature and methanol was added to it. The reaction mass was stirred for next 30 minutes and precipitated solid mass was filtered through buchner funnel and washed with methanol. All the filtrates were combined and suitably diluted. The product from aqueous solution was extracted in toluene. Combined toluene extracts was washed with 2% aqueous NaOH solution under stirring for 30 minutes. The toluene layer was separated and washed with water. Toluene layer was dried over sodium sulfate, filtered and evaporated at reduced pressure to get solid residue. The solid residue was treated with MTBE to get 3.0 gm solid product. HPLC Purity: 97%.

EXAMPLE 2

Process for the Preparation of
6-Methylen-androst-1,4-diene-3,17-dione
(Exemestane)

6-Methylen-androst-4-ene-3,17-dione (200 g) was dissolved in N-methyl pyrrolidine (600 mL) at RT & to it was charged Chloranil (330 g) at RT. The reaction mass was heated to 75 to 80° C. for 15 hours. The progress of the reaction was monitored on TLC. The reaction mass was cooled to room temperature and methanol was added to it. The reaction mass was stirred for 30 minutes and precipitated solid mass was filtered through Buchner funnel and washed with methanol. All the filtrates were combined and water was added to it. The product from aqueous solution was extracted with toluene. Combined toluene extracts were washed twice with 6% aqueous $K_2CO_3$ solution under stirring for 2 hours. The toluene layer was separated and washed with water. Toluene layer was dried over sodium sulfate, filtered and evaporated at reduced pressure to get solid residue. The solid residue was treated with MTBE (600 mL) to get 111 g solid product (Exemestane—crude). HPLC Purity: 97.5%

EXAMPLE 3

Process for the Preparation of
6-Methylen-androst-1,4-diene-3,17-dione
(Exemestane)

6-Methylen-androst-4-ene-3,17-dione (100 g) dissolved in N-methylpyrrolidine (300 mL) at RT, charge Chloranil (165 g) in to the reaction mixture at RT and heat the reaction mass to 75 to 80° C. for 15 hours. The progress of the reaction was monitored on TLC. The reaction mass was cooled to room temperature and methanol was added to it. The reaction mass was stirred for 30 minutes and precipitated solid mass was filtered through Buchner funnel and washed with methanol. All the filtrates were combined and water was added to it. The product from aqueous solution was extracted with toluene. Combined toluene extracts were washed with 2% aqueous NaOH solution under stirring for 2 hours. The toluene layer was separated and washed with water. Toluene layer was dried over sodium sulfate, filtered and evaporated at reduced pressure to get solid residue. The solid residue was treated with MTBE (200 mL) to get 55 g solid product (Exemestane—Crude). HPLC Purity: 97.3%

EXAMPLE 4

Process for the Preparation of
6-Methylen-androst-1,4-diene-3,17-dione
(Exemestane)

6-Methylen-androst-4-ene-3,17-dione (25 g) was dissolved in N-methyl pyrrolidine (75 mL) at RT & to it was charged Chloranil (41.25 g) at RT. The reaction mass was heated to 100 to 110° C. for 2 hours. The progress of the reaction was monitored on TLC. The reaction mass was cooled to room temperature and methanol was added to it. The reaction mass was stirred for 30 minutes and precipitated solid mass was filtered through Buchner funnel and washed with methanol. All the filtrates were combined and water was added to it. The product from aqueous solution was extracted with toluene. Combined toluene extracts were washed twice with 6% aqueous $K_2CO_3$ solution under stirring for 2 hours. The toluene layer was separated and washed with water. Toluene layer was dried over sodium sulfate, filtered and evaporated at reduced pressure to get solid residue. The solid residue was treated with MTBE (75, mL) to get 11 g solid product (Exemestane—crude). HPLC Purity: 95.3%

EXAMPLE 5

First Purification of Exemestane.

Crude Exemestane (54.5 g) is suspended in Acetonitrile (163.5 mL) and refluxed for 30 minutes. The solution was cooled down to RT and stirred for 1 hour. The solid product was filtered and washed with acetonitrile. The solid product was dried at 75° C. to 80° C. for 24 hrs to get Exemestane (43.5 g). HPLC Purity: 99.27%.

EXAMPLE 6

Second Purification of Exemestane.

Exemestane (42.5 g) is suspended in acetonitrile (127.5 mL) and refluxed for 30 minutes. The solution was cooled down to RT and stirred for 1 hour. The solid product was filtered and washed with acetonitrile. The solid product was dried at 75° C. to 80° C. for 24 hrs to get Exemestane (38.5 g), HPLC Purity: 99.69%.

EXAMPLE 7

Third Purification of Exemestane in Acetonitrile.

Exemestane (37.5 g) is suspended in acetonitrile (750 mL) and heated at 65° C. to 70° C. to get clear solution. Charged activated charcoal (3.75 g) to the solution and maintained stirring for 1 hr. The solution was filtered through hyflow bed at 65° C. to 70° C. and hyflow bed was washed with fresh acetonitrile (20 mL). Filtrate was transferred to distillation unit and approximately 670 mL of solvent was distilled out. The remaining solution was cool down to 25° C. to 35° C. and stirred for 1 hr. The solid product was filtered and washed with acetonitrile. The solid product was dried at 75° C. to 80° C. under vacuum for 24 hrs to get Exemestane (34.2 g), HPLC Purity: 99.89%.

EXAMPLE 8

Process for the Purification of Exemestane in Methanol.

Crude Exemestane (50 g) is suspended in methanol (150 mL) and refluxed for 30 minutes. Cool down the solution at RT and stirred for 1 hour. The solid product was filtered and washed with methanol. The solid product was dried at 60° C. to 65° C. for 2 hrs to get Exemestane (35.7 g). The further purification may be done by process similar to the one disclosed above.

We claim:
1. A process for preparing 6-Methylen-androst-1,4-diene-3,17-dione (I), which comprises the steps of:

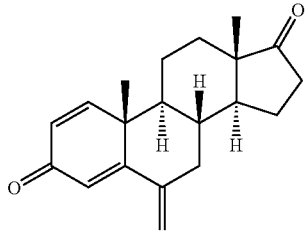

reacting 6-Methylen-androst-4-ene-3,17-dione (II)

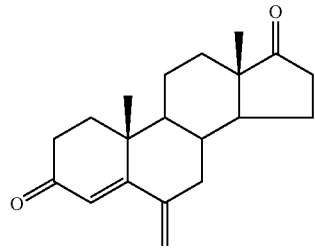

AD-6-Methylene with chloranil in solvent, wherein said solvent is selected from N-methylpyrrolidine and dimethyl sulfoxide or a mixture thereof.

2. The process as claimed in claim 1, wherein oxidizing is agent charged in to the reaction mixture at room temperature.

3. The process as claimed in claim 1, wherein the reaction is carried out at temperature in a range from 50-120° C.

4. The process as claimed in claim 3, wherein the reaction is carried out at temperature in the range of 80 to 110° C.

5. The process as claimed in claim 1, wherein the reaction mixture is refluxed for 1-20 hours.

6. The process as claimed in claim 5 wherein the reflux time is 10-18 hours.

7. A process of purification of 6-Methylen-androst-1,4-diene-3,17-dione (I) prepared according to claim 1 comprising repeated recrystallization from acetonitrile, methanol or a mixture thereof.

8. The process according to claim 1, wherein the solvent is N-methylpyrrolidine.

* * * * *